United States Patent [19]

Stern et al.

[11] 4,264,515

[45] Apr. 28, 1981

[54] PROCESS FOR MANUFACTURING A N-ACYL α-AMINO ACID

[75] Inventors: Robert Stern, Paris; Andre Hirschauer, Montesson; Dominique Commereuc, Meudon; Yves Chauvin, Le Pecq, all of France

[73] Assignee: Institut Francais du Petrole, Rueil-Malmaison, France

[21] Appl. No.: 103,774

[22] Filed: Dec. 14, 1979

Related U.S. Application Data

[63] Continuation-in-part of Ser. No. 917,753, Jun. 21, 1978, abandoned.

[30] Foreign Application Priority Data

Jun. 21, 1977 [FR] France ................. 77 19213

[51] Int. Cl.$^3$ ........................................... C07C 102/00
[52] U.S. Cl. ..................................... 260/404; 560/41; 560/171; 562/450; 562/522
[58] Field of Search .............. 562/522, 450; 560/41, 560/171; 260/404

[56] References Cited

U.S. PATENT DOCUMENTS 2,820,059  1/1958  Hasek ........................... 260/604 HF
2,834,812  5/1958  Hughes ......................... 260/604 HF
3,766,266  10/1973  Wakamatsu ...................... 562/518

FOREIGN PATENT DOCUMENTS 1414910  11/1975  United Kingdom.
1484953  9/1977  United Kingdom.

OTHER PUBLICATIONS

Fell, Tetrahedron Letters, p. 3261, (1968).
Ullmanns, "Encyklopaedieder Technischen Chemie," Chem. vol. 7, p. 122.
Abst. 52:14661 (1958).
Wakamatsu, J. Chem. Soc., D, p. 1540, (1971).
Murachashi, Bull. Chem. Soc., Jap., 33, pp. 78–80 (1960).

*Primary Examiner*—Natalie Trousof
*Assistant Examiner*—Michael Shippen
*Attorney, Agent, or Firm*—Millen & White

[57] ABSTRACT

A N-acyl α-amino acid is manufactured by reacting an unsaturated vegetable oil or a $C_8$–$C_{30}$ mono-olefinic compound with an amide, carbon monoxide and hydrogen, in the presence of a cobalt catalyst. The process is operated in one step, providing for an increased selectivity as compared with a two-step process.

12 Claims, No Drawings

PROCESS FOR MANUFACTURING A N-ACYL α-AMINO ACID

STATUS OF THE APPLICATION

This application is a continuation-in-part of our prior application Ser. No. 917,753, now abandoned.

BACKGROUND OF THE INVENTION

The present invention relates to a one-step process for manufacturing selectively higher N-acyl α-amino acids by reaction of a mono-olefinic compound with carbon monoxide, hydrogen and an amide.

It is highly advantageous to manufacture higher N-acyl α-amino acids in one step, particularly those having the amino acid grouping in terminal position. These products are not only precursors of amino acids, since they can be converted to amino acids by hydrolysis but they are also bases for industrial and medicinal products.

Certain compounds of the acetylamino tetradecanoic acid type are anti-carcinogenic agents. The acetylated amino acids increase the softening properties of soaps, i.e. they decrease their alkalinity. The sodium salts of long chain N-acyl amino acids have anticorrosion properties with respect to steels. Certain esters of acylamino acids have herbicidal properties. Above all, the esters and sodium salts of the N-acyl amino acids have known detergent properties. They can be used for making microemulsions, which can be used, for example, in secondary or tertiary oil recovery. Gel properties may be obtained by esterification or acylation of amino acids with a second carboxylic group, and the resultant materials are useful for shampoos, paints or for recovering oil from polluted waters. Certain N-acyl amino acids are metal chelatants. There are thus many possible uses, although not widespread up to now, since the manufacturing price of higher amino acids having the amino acids group in terminal position was up to now relatively high. It was also difficult to obtain these amino acids, particularly those having a long straight chain.

THE PRIOR ART

A method is disclosed in U.S. Pat. No. 3,766,266, which comprises the reaction of an aldehyde with carbon monoxide in the presence of an amide to obtain a N-acyl α-amino acid. It is also stated that the aldehyde may be formed in situ in a preliminary reaction or simultaneously with the main reaction. Examples of reactions allowing aldehyde formation are the isomerization of an epoxy compound, the hydrogenation of an acid anhydride or the hydroformylation of an olefin.

The first two reactions are illustrated by examples according to which the main reaction, which is the object of said patent specification, is performed simultaneously with the secondary reaction which produces the aldehyde, but this is not the case for aldehyde formation from olefins. In the letter case, the aldehyde is first produced in a distinct step, according to a known process, and the resulting aldehyde mixture is then reacted with acetamide and carbon monoxide.

The particular olefinic compound used in the latter case was methyl acrylate which yields two aldehydes. The two aldehydes are converted to a mixture of N-acyl amino acids, which is said to consist of 88% straight-chain acid and 12% branched-chain acid.

It could be expected that the same reaction, if applied to simple olefins, would not give such high selectivities, since it is known that simple mono-olefins yield a mixture of 70-75% of linear aldehydes and 30-25% of branched aldehydes when subjected to hydroformylation.

It has been found by the applicants that, when trying to apply the process of the above patent to simple olefins such as 1-butene, the selectivity to straight-chain N-acyl amino acid was poor, in any case below about 75%.

It is thus clear that, when starting from a simple olefin and operating as in said prior patent specification, it is not possible to obtain a single amino acid, but rather several amino acids which must be separated later, which necessitates an expensive additional step. This explains why the authors of the prior patent specification have not explored this path, except in the special case of methylacrylate, and have preferred to make use of a previously purified aldehyde.

THE INVENTION

It has surprisingly been discovered that far higher selectivities are obtained when working in one step with higher mono-olefinic compounds and that the two-step reaction, when applied to the same compounds, does not give these high selectivities.

It is highly advantageous to obtain terminal (end-chain) N-acyl amino acids either pure or as mixtures containing more than about 85% of the terminal (end-chain) isomeric acid since these mixtures may be purified easily, for example, by crystallization. Difficulties appear when the selectivity is below 85% since the yield of the purification greatly decreases.

By terminal N-acyl amino acid, there is meant a compound having a glycyl group

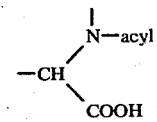

linked directly through its CH group to a R—CH$_2$—group (thus a terminal group) of an organic compound, in contrast to the isomeric compounds where the CH group of the glycine group is linked to a

group (thus an internal group), R and R' being alkyl groups. The terminal N-acyl amino acids, particularly those having a long straight-chain of, for example, at least 8 carbon atoms, have distinctive properties, for example, easier bio-degradability, which is important particularly for surfactants.

Although no quite satisfactory explanation of these advantageous results has been found up to now, some additional experiments tend to show that the mechanism of the reaction is not the same when operating in one step or in two steps. For example, when operating in two steps, there is formed, in addition to the isomeric N-acyl amino acids, by-products of hydroformylation or hydrogenation such as alcohols acetals, aldols, formates, polymers, or lactones in the case of acrylates, whereas the formation of these by-products is avoided to a large extent when proceeding in one single step.

Finally, in the reaction of the present the invention, the process for manufacturing amino acids is made selective and economically attractive, which was not the case when starting with an aldehyde or even with a low molecular weight olefin.

The process of the invention comprises the simultaneous raction of an olefinic compound selected from the unsaturated vegetable oils and compounds having from 8 to 30 carbon atoms, preferably an α-olefin with 8-20 carbon atoms, with an amide, hydrogen and carbon monoxide.

The starting olefinic compound is preferably of the formula:

$$R_1-\underset{\underset{R_2}{|}}{C}=CHR_3$$

where each of $R_1$, $R_2$ and $R_3$ may be hydrogen, alkyl or alkenyl of 1-28 carbon atoms or one of $R_1$ and $R_3$ may be carboxyalkyl or carboxyalkenyl-$R_6$-COOH or carbalkoxyalkyl or carbalkoxyalkenyl-$R_6$-COOR$_7$ with $R_7$ being alkyl of 1-28 carbon atoms and $R_6$ being alkylene or alkenylene of 1-28 carbon atoms, provided the starting olefinic compound has a total of 8 to 30 carbon atoms. Thus both terminal and internal olefinic compounds may be used.

For example, each of $R_1$, $R_2$ and $R_3$ may be hydrogen, alkyl of 1-22 carbon atoms or a—$(CH_2)_n$—X group where n=1 to 22 and X is a carboxyl ester group.

A preferred class of olefinic compounds comprises the α-monoolefinic hydrocarbons with 8-20 carbon atoms.

The starting amide is preferably of the formula:

$$R_4 NH-CO-R_5$$

where each of $R_4$ and $R_5$ may be hydrogen or alkyl of 1-28 carbon atoms. $R_5$ may also be aryl of 6-12 carbon atoms. Preferably $R_4$ is hydrogen or an alkyl group with 1-22 carbon atoms and $R_5$ is hydrogen or an alkyl group with 1-20 carbon atoms.

Under the proviso that the olefinic compound has 8-30 carbon atoms, $R_1$, $R_2$ and $R_3$ may be, for example hydrogen, methyl, propyl, dodecyl, hexadecyl, or one of $R_1$ and $R_3$ may be 2-carboxyethyl, 14-carboxytetradecyl, 16-methoxycarbonylhexadecyl or 16-glyceryloxycarbonylhexadecyl (in that case the olefinic compound may be an unsaturated vegetable oil).

Examples of $R_4$ and $R_5$ are hydrogen, methyl, ethyl, dodecyl and hexadecyl.

The catalysts are, as a rule, cobalt-containing compounds or complexes, to which other metals may be added, such as rhodium, palladium or ruthenium, as co-catalysts.

Among the cobalt compounds are the inorganic or organic cobalt salts and dicobalt octacarbonyl (cobalt tetracarbonyl). The cobalt salt may be an inorganic salt, for example, cobalt iodide, although cobalt carboxylates are preferred, such as cobalt formate, acetate, butyrate, naphthenate, oleate or stearate. Co-catalysts such as phosphines, amines or sulfur derivatives may be added to cobalt carbonyl. The phosphines are tertiary phosphines, for example, aromatic or aliphatic phosphines. Examples of amines are tertiary amines and heterocyclic amines such as pyridine. Dimethyl sulfide is an example of a sulfur compound. Catalysts soluble in the reaction medium are preferred; however Raney cobalt may be the starting material. The amount of catalyst is, for example, 0.01 to 5% by weight of the olefinic compound, calculated as cobalt.

The reaction is preferably operated in an inert solvent. Preferred inert solvents are those which permit at least partial dissolution of the amide and the olefinic compound. These are generally polar solvents, for example of the ester, ether, ketone, amide, sulfoxide or aromatic hydrocarbon type. The solvent may be omitted in certain cases, when, for example, the reactant olefinic compound is an unsaturated acid or ester, for example, undecylenic acid, oleic acid or a vegetable oil. Examples of oils are soybean oil, sunflower oil, peanut oil, palm oil, rape-seed oil, Primor rape-seed oil or fats like tallow.

The amount of solvent, when used, is preferably from 0.5 to 20 parts by weight per part by weight of the olefinic compound.

Methyl and ethyl acetate are examples of solvents. Other polar solvents are ethers, such as dioxane, methyl tert.-butyl ether, methyl tert.-amyl ether, or tetrahydrofuran, tertiary amides, such as dimethyl formamide, dimethyl sulfoxide and ethylene carbonate.

Ether solvents are preferred and appear to have a positive effect on the selectivity.

The molar ratio of the olefinic compound to the amide is preferably the stoichiometric ratio, i.e. 1:1, although it may be advantageous to use an excess of one of the reactants, so that said ratio may range, for example, from 10:1 to 1:10. It has been surprisingly found that the yield to amide of one single type is maximum when operating with an amide deficiency (there is then used 0.5 to 0.8 mole of amide per mole of olefin).

It is advantageous to use CO and $H_2$ in excess of the stoichiometric amount, this excess being easily recoverable at the end of the reaction.

The starting olefinic compound may be, for example, 1-octene, 2-octene, 2-methyl-1-heptene, 1-hexadecene, a mixture of $C_{22}$-$C_{26}$ olefins complying with the above general formula, methyl oleate, glyceryl trioleate, oleic acid or vegetable oils such as soybean, palm or rape-seed oil or animal fats. Higher olefins, for example, $C_8$ to $C_{20}$ α-olefins may yield detergents, bactericides or gelling agents.

The starting amide may be, for example, formamide, acetamide, propionamide, butyramide, stearyl amide or N-methyl acetamide.

The operating conditions may be selected in a wide range. The total pressure may be, for example, 10 to 250 atmospheres, for example 30 to 200 atm. It appears that higher selectivities are obtained when operating at moderate pressures, in the range from 70 to 150 atm. The $H_2$ to CO ratio is, for example, 5:1 to 1:10 and preferably 1:1 to 1:2 by mole. It is generally advantageous not to increase the $H_2$/CO ratio too much to avoid alcohol formation. It is however possible to operate with reversed ratios, for example 2:1, particularly at lower temperature. The temperatures are usually from 50° to 200° C. The highest selectivity is obtained at temperatures of 50° to 110° C.

In certain cases, the solvent may take part in the reaction. Thus certain alcohols react with the N-acyl amino acids to form esters thereof. Since it seems that these solvents decrease the reaction rate somewhat, their use should be avoided whenever possible.

The N-acylamino acid usually crystallizes by mere cooling of the reaction medium which constitutes an easy way to isolate the product. Other methods may be used.

The resulting product may contain unreacted materials. It is easy to separate the olefinic compound from the N-acylamino acid, either by vaporization of the olefin or by extraction after solvent vaporization. The solvents to be used for extracting the olefins are usually saturated or unsaturated hydrocarbons. The n-acylamino acid may also be neutralized with, for example, sodium or potassium hydroxide; the N-acylamino acid generally passes into the aqueous phase The N-acylamino acids are often insoluble in the aqueous phase. This permits to separation of the cobalt catalyst which may dissolve into the aqueous phase, with or without prior acidification. The acids may be organic or inorganic. Certain acids such as oxalic acid and citric acid yield precipitates in the organic phase.

The following examples where the olefinic compound and the amide are in liquid phase are illustrative and not limitative of the invention.

EXAMPLE 1

A mixture of 0.1 mole of an olefin as disclosed in Table I and 0.1 mole (5.6 g) of acetamide in 80 ml dioxane was introduced into an autoclave provided with a mechanical stirrer. The autoclave was scavenged with nitrogen and 250 mg of cobalt tetracarbonyl was added. Then the pressure was raised to about 100 kg/cm2 with a mixture of CO+H$_2$ in a molar ratio of 1:1. The autoclave was then sealed and heated to 100°–110° C., at which temperature the initial pressure was about 130 kg/cm2.

After about 2 hours at 100°–110° C., the pressure had decreased to 100 kg/cm2 and no more gas was absorbed; it was noted that approximately 0.3 mole of gas had been absorbed. Stirring was then discontinued and the autoclave was cooled and opened for analysis.

The yield of crude N-acetylamino acid with respect to the olefin was estimated by titration with a solution of sodium hydroxide in ethanol.

A sample of the product was esterified with n-butanol and the resultant product was analyzed by vapor phase chromatography and nuclear magnetic resonance (NMR) spectrometry to determine the ratio of the straight chain N-acetylamino acid to the branched chain N-acetylamino acid. The end-chain structure of the N-acetyl amino acid is determined by compression of the integrals of the signals obtained by NMR at 0.85 ppm (CH$_3$-R) and 2.1 ppm (CH$_3$-CO). The "end-chain" compound has one -CH$_3$ group less than the isomeric "internal" compound.

Table I summarizes the results (the results obtained with 1-butene are given for comparison).

TABLE I

| Olefin | crude N-acetyl amino acid: yield (%) | end-chain isomer: internal isomer ratio in the crude product |
|---|---|---|
| 1-octene | C$_{10}$ acid : 72 | 9 : 1 |
| 1-dodecene | C$_{14}$ acid : 73 | 11.5 : 1 |
| 1-hexadecene | C$_{18}$ acid : 76 | 13.2 : 1 |
| 1-tetracosene | C$_{26}$ acid : 72 | 12 : 1 |
| 1-butene | C$_6$ acid : 78 | 2.0 : 1 |

A sample of the product obtained from dodecene was twice recrystallized from in acetone and found to melt at 94°–96° C. By NMR it was found it consisted of about 98% of the straight-chain N-acetyl α-amino tetradecanoic acid $$CH_3-(CH_2)_{11}-CH\diagup^{COOH}_{\diagdown NHCOCH_3}$$

COMPARATIVE EXAMPLE 1A

The operation was conducted in two steps: first hydroformylation and then reaction with an amide.

0.1 mole of olefin and 80 ml of dioxane were introduced into the same autoclave as in Example 1. After scavenging with nitrogen, 250 mg of cobalt tetracarbonyl was introduced. The pressure was raised to about 100 kg/cm2 with a mixture of CO=H$_2$ in a molar ratio of 1:1. The autoclave was then heated to 100°–110° C., at which temperature the initial pressure was about 130 mg/cm2.

After about 1.5 hours no more gas was absorbed and the pressure was about 110 kg/cm2. After cooling, 0.1 mole acetamide was added and the pressure raised again to 100 Kg/cm2 (at room temperature) with the same 1:1 mixture of CO and H$_2$. After heating to 100°–110° C., the initial pressure was again 130 kg/cm2. After 3 hours the gas absorption ceased, the pressure was 121 kg/cm2, and the autoclave was cooled and opened for analysis.

The yield and the structure of the products are given in Table II.

TABLE II

| Olefin | crude N-acetyl amino acid: yield (%) | end-chain isomer: internal isomer ratio in the crude product |
|---|---|---|
| 1-octene | C$_{10}$ acid : 37 | 3.0 : 1 |
| 1-dodecene | C$_{14}$ acid : 35 | 2.4 : 1 |
| 1-hexadecene | C$_{18}$ acid : 33 | 2.8 : 1 |
| 1-tetracosene | C$_{26}$ acid : 31 | 3.0 : 1 |

EXAMPLE 2

Example 1 is repeated, except that the starting olefin is a C$_{12}$ mono-olefins mixture whose content of internal olefins is 97%, the double bonds being distributed throughout positions 2 to 6.

The yield of crude C$_{14}$ N-acetylamino acid is 68% and the ratio of the end-chain isomer to the internal isomers is 20:1.

It is to be noted that simple hydroformylation of the same mono-olefins yields an aldehyde mixture comprising about 55% of the end-chain aldehyde and 45% of the internal aldehyde.

EXAMPLE 3

Example 1 is repeated with 1-dodecene except that the amide is laurylamide (0.1 mole).

The yield of crude product is 65%. The ratio of the end-chain C$_{14}$ N-lauryl aminoacid to the internal isomer is 10:1.

EXAMPLE 4

Example 1 is repeated with 1-dodecene except that only 0.05 mole acetamide is used. The yield of crude C$_{14}$ N-acetylamino acid is 90% and the ratio of the end-chain compound to the internal compound is 15:1.

EXAMPLE 5

A mixture of 672 g of 1-dodecene (4 moles), 256 g of acetamide (about 4 moles), 1.6 liters of dioxane, 1.05 g cobalt carbonyl and 10 g cobalt acetate are introduced into a 5-liter autoclave. A 100 kg/cm2 pressure of CO and $H_2$ is applied (molar ratio of 1:1). The temperature is raised to 110° C. The reaction starts and cooling is applied to maintain the temperature at 95°–100° C. The CO+$H_2$ mixture is recycled several times, so that the pressure falls from 150 to 80 kg/cm2. After 5 hours the gas mixture is no longer absorbed. The crude product contains only 0.2% of olefin. The catalyst is separated and the solid material is filtered and/or dissolved into acetone. After two crystallizations, 485 g of N-acetyl α-aminotetradecanoic acid are obtained. The mother-liquors contain 1.2 mole of N-acetylamino acid, thus 825 g as total. The molar yield is 73%. The product melts at 95° C.

A typical elemental analysis of the product gave the following results observed C=67.18, H=10.94, N=4.83
calculated C=67.4, H=10.8, N=4.92.

By NMR (nuclear magnetic resonance), it is appreciated that about 98% of a single linear isomer is present; its formula is:

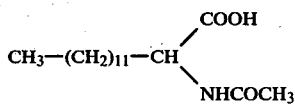

COMPARATIVE EXAMPLE 6

33.6 g of 1-dodecene, 500 mg of cobalt carbonyl and 80 ml of dioxane was admixed in an autoclave and a 100 kg/cm2 pressure of carbon monoxide and hydrogen is applied, the ratio CO:$H_2$ being 1:1. The temperature is 100°–110° C. The hydroformylation reaction takes 2 hours, including heating, cooling, gas purging and sample withdrawing. A second reaction is then performed: 10 g of acetamide and 0.5 g of cobalt carbonyl are added and the pressure of 100 kg/cm2 is again applied (CO:$H_2$=1:1 by mole). A product is obtained after 1.5 hours at 100° C. Analysis of the first reaction by vapor phase chromatography (VPC) shown that in the first operation, 91% of olefin has been converted. The aldehydes are analyzed by VPC and 71% of end-chain aldehydes is found, with respect to all the aldehydes present. 7.8% of alcohols is also found, with respect to both aldehyde and alcohol.

The second reaction yields N-acetyl $C_{14}$ aminoacids which may be isolated by crystallization and analyzed by NMR. The elemental analysis is that of an acetamido tetradecanoic acid. Two isomers are found by NMR: 73% of the whole aminoacid content corresponds to the end-chain acid, the remainder corresponding to the internal aminoacid. The aminoacid yield is 47% with respect to the aldehydes. This example shows the complexity of a two-step operation, the presence of by-products which decrease the yield of the first step, the poor selectivity and the low yield in the second step.

EXAMPLE 7

An autoclave is charged with 56.4 g commercial oleic acid containing by weight: 71% oleic acid, 12% linoleic acid, 6% palmitoleic acid and 11% saturated acids. 11.8 g acetamide, 80 ml dioxane and 10 ml of cobalt carbonyl solution in hexane (500 mg $Co_2(CO)_8$) is added to the mixture of acids. The temperature is 150° C., the pressure 100 kg/cm2 and the CO:$H_2$ ratio 2:1. The reaction is fast. After 2 hours, only traces of acetamide are present. The conversion to the acyl derivative is 70%. After hydrolysis with sodium hydroxide and re-acidification, the product melts at 150°–160° C.; it contains, an average of 2 acid groups per molecule. The sodium and potassium salts have detergent properties.

What we claim is:

1. In a process for manufacturing an N-acyl α-amino acid in a reaction catalyzed by a cobalt carbonylation catalyst, the improvement which comprises reacting in one step a mixture of (a) at least one olefinic compound selected from unsaturated vegetable oils and compounds of the formula $$R_1R_2C=CHR_3$$

wherein each of $R_1$, $R_2$ and $R_3$ is hydrogen, alkyl or alkenyl of 1–28 carbon atoms, or one of $R_1$ and $R_3$ is —$R_6$—COOH or —$R_6$—$COOR_7$ wherein $R_6$ is alkylene or alkenylene of 1–28 carbon atoms and $R_7$ is alkyl of 1–28 carbon atoms, with the proviso that each olefinic compound of the formula $R_1R_2C=CHR_3$ has a total of 8 to 30 carbon atoms, (b) at least one amide of the formula $$R_4NH-CO-R_5$$

where $R_4$ and $R_5$ are each hydrogen or an alkyl group of 1–28 carbon atoms, or $R_5$ is an aryl group 6–12 carbon atoms, (c) carbon monoxide, and (d) hydrogen, in contact with said cobalt catalyst.

2. A process according to claim 1, wherein said at least one olefinic compound has the formula $R_1R_2C=CHR_3$ and each of $R_1$, $R_2$ and $R_3$ is hydrogen, alkyl of 1–22 carbon atoms or a —$(CH_2)_n$—X group where n is 1 to 22 and X is a carboxyl group or a carboxylic ester group, and wherein $R_4$ is hydrogen or an alkyl group of 1–22 carbon atoms and $R_5$ is hydrogen or an alkyl group of 1–20 carbon atoms.

3. A process according to claim 1, wherein the olefinic compound is an α-minoolefinic hydrocarbon of 8 to 20 carbon atoms.

4. A process according to claim 1, wherein the reaction is effected at a temperature of from 50° to 200° C., and a pressure of from 30 to 200 atm.

5. A process according to claim 4, wherein the pressure is from 70 to 150 atm.

6. A process according to claim 4, wherein the temperature is from 50° to 110° C.

7. A process according to claim 1, wherein the reaction is effected in an ether solvent used in an amount of 0.5 to 20 weight parts per part by weight of the olefinic compound.

8. A process according to claim 7, wherein said solvent is dioxane.

9. A process according to claim 1, wherein the cobalt catalyst is used as a mixture with a rhodium carbonylation catalyst.

10. A process according to claim 1, wherein the cobalt catalyst is cobalt carbonyl.

11. A process according to claim 1, wherein the proportion of amide is 0.5 to 0.8 mole per mole of olefinic compound.

12. A process according to claim 1, wherein the cobalt catalyst is present in an amount of 0.01 to 5%, calculated as cobalt, by weight of the olefinic compound.

* * * * *

UNITED STATES PATENT AND TRADEMARK OFFICE
CERTIFICATE OF CORRECTION

PATENT NO. : 4,264,515
DATED : April 28, 1981
INVENTOR(S) : Robert Stern et al

It is certified that error appears in the above—identified patent and that said Letters Patent is hereby corrected as shown below:

Column 8, line 28: reads "1-28 carbon atoms, or $R_5$ is an aryl group 6-12 carbon"
should read -- 1-28 carbon atoms, or $R_5$ is an aryl group of 6-12 carbon -- .

Column 8, line 42: reads "compound is an α-minoolefinic hydrocarbon of 8 to"
should read -- compound is an α-monoolefinic hydrocarbon of 8 to -- .

Signed and Sealed this

Thirtieth Day of June 1981

[SEAL]

Attest:

RENE D. TEGTMEYER

Attesting Officer　　Acting Commissioner of Patents and Trademarks